US008702680B2

(12) United States Patent
Jimenez et al.

(10) Patent No.: US 8,702,680 B2
(45) Date of Patent: Apr. 22, 2014

(54) DOUBLE HELIX REINFORCED CATHETER

(71) Applicant: Depuy Synthes Products, LLC, Raynham, MA (US)

(72) Inventors: Oscar Jimenez, Coral Gables, FL (US); Roberto Echarri, Miami, FL (US); Kenneth Verduin, Coral Springs, FL (US)

(73) Assignee: Depuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/738,154

(22) Filed: Jan. 10, 2013

(65) Prior Publication Data

US 2013/0131641 A1  May 23, 2013

Related U.S. Application Data

(63) Continuation of application No. 13/046,687, filed on Mar. 11, 2011, now Pat. No. 8,366,699, which is a continuation of application No. 11/433,390, filed on May 12, 2006, now Pat. No. 7,905,877.

(51) Int. Cl.
 *A61M 25/00* (2006.01)

(52) U.S. Cl.
 USPC ..................... 604/524; 604/526; 604/527

(58) Field of Classification Search
 USPC ................................. 604/524–527
 See application file for complete search history.

(56) References Cited

U.S. PATENT DOCUMENTS

| | | |
|---|---|---|
| 3,346,761 A | 10/1967 | Ackerman |
| 3,485,234 A | 12/1969 | Stevens |
| 4,044,765 A | 8/1977 | Kline |
| 4,402,684 A | 9/1983 | Jessup et al. |
| 4,430,083 A | 2/1984 | Ganz et al. |
| 4,454,725 A | 6/1984 | Cann et al. |
| 4,516,972 A | 5/1985 | Samson |
| 4,581,390 A | 4/1986 | Flynn et al. |
| 4,636,346 A | 1/1987 | Gold et al. |
| 4,737,153 A | 4/1988 | Shimamura et al. |
| 4,842,590 A | 6/1989 | Tanabe et al. |
| 4,955,862 A | 9/1990 | Sepetka et al. |
| 5,019,057 A * | 5/1991 | Truckai ..................... 604/527 |
| 5,156,155 A | 10/1992 | King et al. |
| 5,234,416 A | 8/1993 | Macaulay et al. |
| 5,279,596 A | 1/1994 | Castaneda et al. |

(Continued)

*Primary Examiner* — Manuel Mendez
*Assistant Examiner* — Gerald Landry, II
(74) *Attorney, Agent, or Firm* — Fulwider Patton LLP

(57) ABSTRACT

The intravascular catheter has two segments; a proximal segment with high stiffness and a distal segment with lower stiffness. The catheter can also have an intermediate segment of lower stiffness than the proximal segment and higher stiffness than the distal segment. The catheter comprises a polymeric inner tube, a reinforcing inner jacket which is spirally wound over the inner tube and which becomes progressively softer from a proximal end to a distal end, and a polymeric outer sheath extruded over the inner jacket according to the teachings of U.S. Pat. No. 5,445,624. The reinforcing jacket comprises helical coiled wires or fibers of various materials and layers wound over the inner tube in order to provide improved multi-axial mechanical properties, such as torque, compression, tension and anti-kinking characteristics. Stainless steel, carbon, glass, platinum, platinum/tungsten or palladium wire in either oval, round or flat geometry are used together with single or dual layers to achieve a graduated stiffness with the reinforcing jacket being stiffer at a proximal end and softer at a distal end. Methods for making the catheter and for annealing ends of the wound wire are also disclosed.

2 Claims, 6 Drawing Sheets

(56) References Cited

U.S. PATENT DOCUMENTS

| | | | |
|---|---|---|---|
| 5,308,342 A | 5/1994 | Sepetka et al. | |
| 5,338,296 A | 8/1994 | Dalessandro et al. | |
| 5,382,234 A | 1/1995 | Cornelius et al. | |
| 5,445,624 A | 8/1995 | Jimenez et al. | |
| 5,454,795 A | 10/1995 | Samson et al. | |
| 5,458,605 A | 10/1995 | Klemm et al. | |
| 5,526,849 A | 6/1996 | Gray | |
| 5,554,139 A | 9/1996 | Okajima et al. | |
| 5,569,200 A | 10/1996 | Umeno et al. | |
| 5,695,483 A | 12/1997 | Samson et al. | |
| 5,702,373 A | 12/1997 | Samson et al. | |
| 5,782,809 A | 7/1998 | Umeno et al. | |
| 5,816,923 A | 10/1998 | Milo et al. | |
| 5,879,342 A | 3/1999 | Kelley et al. | |
| 5,891,114 A * | 4/1999 | Chien et al. | 604/527 |
| 5,947,940 A | 9/1999 | Beisel et al. | |
| 5,951,539 A * | 9/1999 | Nita et al. | 604/526 |
| 6,152,912 A * | 11/2000 | Jansen et al. | 604/526 |
| 6,165,163 A | 12/2000 | Chien et al. | |
| 6,177,682 B1 | 1/2001 | Bartulovic et al. | |
| 6,210,396 B1 | 4/2001 | MacDonald et al. | |
| 6,290,692 B1 | 9/2001 | Klima et al. | |
| 6,508,804 B2 | 1/2003 | Sarge et al. | |
| 6,616,996 B1 * | 9/2003 | Keith et al. | 428/35.8 |
| 6,824,553 B1 | 11/2004 | Samson et al. | |
| 7,104,979 B2 | 9/2006 | Jansen et al. | |
| 7,831,311 B2 | 11/2010 | Cross, Jr. et al. | |
| 7,850,623 B2 | 12/2010 | Griffin et al. | |
| 2003/0191451 A1 * | 10/2003 | Gilmartin | 604/527 |
| 2004/0002727 A1 | 1/2004 | Hwang et al. | |
| 2005/0004556 A1 | 1/2005 | Pursley | |
| 2006/0095050 A1 * | 5/2006 | Hartley et al. | 606/108 |
| 2008/0306499 A1 * | 12/2008 | Katoh et al. | 606/159 |
| 2009/0240235 A1 * | 9/2009 | Murata | 604/527 |
| 2009/0306587 A1 * | 12/2009 | Milijasevic et al. | 604/95.04 |

* cited by examiner

DOUBLE HELIX REINFORCED CATHETER

CROSS-REFERENCES TO RELATED APPLICATIONS

This is a continuation of U.S. Ser. No. 13/046,687, filed Mar. 11, 2011, now U.S. Pat. No. 8,366,699; which is a continuation of U.S. Ser. No. 11/433,390, filed May 12, 2006, now U.S. Pat. No. 7,905,877, incorporated by reference in its entirety.

BACKGROUND OF THE INVENTION

1. Field of the Invention

The present invention relates to an intravascular catheter having a stiff proximal end portion and gradually softer and more flexible portions progressively toward a distal end of the catheter which is used for diagnostic, interventional and or drug infusion procedures such as blood clot dissolving drugs, chemotherapeutic agents, and injection of contrast media to visualize vasculature and or anatomy using a fluoroscope to assist visualization of the catheter inside the human body. The present intravascular catheter can also be used to deliver coils to aneurisms, and embolic agents to arteriovenous malformation (AVM) in the brain and other parts of the human vasculature such as uterine fibroids. The latter procedure is usually referred to as uterine fibroid embolization (UFE). The present invention more specifically relates to micro catheters for use in interventional neuro radiological procedures where access to brain vasculature is required. Further, the present invention relates to a microcatheter to deploy coils and embolic agents to treat certain brain vasculature syndromes to include but not limited to aneurisms and AVM indications.

2. Description of the Related Art

Intravascular catheters are used to diagnose and treat a number of medical conditions of the vascular system using a technique called angiography. A number of intravascular catheters are used to diagnose coronary artery disease related to stenosis and to determine hemodynamic factors such as cardiac output. In addition, smaller catheters, "micro-catheters", are used to infuse certain blood clot dissolving drugs to the coronaries or to brain blood vessels in stroke related cases. Further, in addition, intravascular catheters are also used to deploy stents in the coronary arteries as well as in the peripheral vasculature; other indications may include but not limited to deployment of embolic agents and coils to target vasculature within the brain and elsewhere in the human body.

In order to properly navigate or manipulate a catheter after introduction in the human vasculature, it is imperative that the intravascular catheter be designed and constructed in such a manner as to facilitate introduction into a blood vessel and to support further manipulations to reach the target blood vessel. Manipulation of the catheter is done by the physician using the proximal segment of the catheter, after catheter introduction and external to the blood vessel; that is, the catheter needs to be rotated (torque) outside the body in the proximal segment of the catheter and a corresponding rotational reaction must be achieved in the distal tip segment inside the body. Therefore, a vascular catheter, to sustain torsional continuity from the proximal end to the distal end of the, while inside the vasculature, must transmit torque from the proximal end to the distal end inside the body. The typical distance between proximal and distal end for vascular catheters ranges between 80-120 centimeters and shorter for renal applications that require a length of approximately 45-55 centimeters; thus, a vascular catheter is required to advance forward when pushed, be able to be retrieved when pulled and to rotate when torque is applied as part of the maneuvering process to reach the target vessel. Another critical characteristic is that the catheter's wall must not collapse (kink) and retain its lumen integrity, cylindrical shape or ovality during the medical procedure.

Heretofore, a number of analogous and non-analogous intravascular catheter constructions have been proposed, as disclosed in the following U.S. Patents:

| Pat. No. | Patentee |
|---|---|
| 3,485,234 | Stevens |
| 4,044,765 | Kline |
| 4,402,684 | Jessup |
| 4,430,083 | Ganz et al. |
| 4,516,972 | Samson |
| 4,581,390 | Flynn |
| 4,636,346 | Gold et al |
| 4,737,153 | Shimamura et al. |
| 4,842,590 | Tanabe et al. |
| 4,955,862 | Septka |
| 5,156,155 | King |
| 5,234,416 | Macauley et al |
| 5,279,596 | Castaneda et al. |
| 5,308,342 | Sepetka et al |
| 5,382,234 | Cornelius et al |
| 5,445,624 | Jimenez |
| 5,454,795 | Samson |
| 5,458,605 | Klemm |
| 5,554,139 | Okajima |
| 5,695,483 | Samson |
| 5,702,373 | Samson |
| 5,569,200 | Umeno et al |
| 5,782,809 | Umeno et al |
| 5,816,927 | Milo et al. |
| 5,879,342 | Kelly |
| 5,947,940 | Beisel |
| 5,951,539 | Nita et al. |
| 6,152,912 | Jansen et al. |
| 6,824,553 | Samson et al. |

BRIEF SUMMARY OF THE INVENTION

The primary objective of the present invention is to provide an intravascular catheter with enhanced physical properties to facilitate maneuverability and efficacy of the catheterization procedure. That is, to provide a reinforced catheter incorporating a double reinforcing coil at the proximal segment with a separate single reinforcing coil at the distal segment whereby the physical properties of the catheter are customized to provide torque (turn ability), axial strength (push ability) while resisting collapsing of the wall (kinking) during manipulation of the catheter through tortuous vasculature. In addition, it is the purpose of this invention to provide a catheter whereby the distal segment exhibits a higher degree of compliance when compared to the proximal segment as provided by the transition from a double coil (proximal) to a single coil (distal) utilizing a different, softer material in the distal single coil. The latter allows for an atraumatic vessel engagement to reduce the incidence of mural trauma, vessel insult or dissection.

Another objective of the present invention is to further refine the physical properties of the catheter by progressively changing the pitch or helical period (picks per inch) so that a continuously, incremental compliance from proximal to distal end is achieved.

It is an additional objective of the present invention to utilize a reinforcing jacket having graduated levels of stiffness along its length to minimize mural trauma associated with stiffer more aggressive catheter designs.

It is a further objective of the present invention to provide a more stable mechanical platform to deploy balloon expandable stents, self expanding stents, micro coils and other interventional devices within the vascular system.

It is an additional objective of the present invention to provide an enhanced mechanical platform utilizing double wire helical coils reinforcement, using either round or flat wire or a combination thereof, that may extend from proximal to distal end, or that can exhibit a transition from a double helical coil to a single coil anywhere along the axis of the intravascular catheter depending on the specific requirements to suit specific medical indication.

Another improvement of the mechanical properties at the distal segment, involves the progressive decrease of the pitch or the helical period (picks per inch) of the reinforcing wire, whereby a continuously progressive compliance of the distal segment is achieved (in a distal direction).

It is a further objective of the present invention to provide a less traumatic intravascular catheter specifically designed for interventional cardiology, interventional neuroradiology and peripheral indications where difficult vasculature challenges a successful catheterization procedure.

It is an additional objective of the present invention to further facilitate the atraumatic deployment of interventional devices into the brain, heart, viscera and peripheral vasculatures using a proximal double helix to distal single helix (coil) in catheter reinforcement.

The present invention relates to an improved intravascular catheter. One improvement relates to the catheter body wherein the body is made of an inner tube incorporating double coil helical wire reinforcement along the surface in a proximal portion of the catheter, the wire geometry being similar to a DNA molecule. This feature provides an improvement in critical mechanical properties such as torque, kink resistance, axial rigidity and distal compliance to reduce the incidence of mural trauma. In one embodiment, the inner tube is made of a high temperature fluorinated polymer having a low coefficient of friction; the inner tube carries in its periphery a plurality of wire reinforcement exhibiting a double helical coil geometry that transitions into a single helical coil at specific point along the axis of the inner tube. The helical wire reinforced inner tube is then jacketed with an outer, low temperature thermoplastic extrusion which is laminated against the double helical coil reinforcement and into the inner tube's surface. The low temperature thermoplastic is interstitially disposed beneath the tangential double and single coil wire reinforcement supported by the inner tube. The outer low temperature thermoplastic may be encapsulated using the teachings of the Jimenez U.S. Pat. No. 5,445,624 entitled "Catheter with Progressively Compliant Tip" in order to further complement the gradual compliance from proximal to distal end.

BRIEF DESCRIPTION OF THE SEVERAL VIEWS OF THE DRAWINGS

Additional objects and advantages of the present invention can be found in the detailed description of the preferred embodiments when taken in conjunction with the accompanying drawings.

DETAILED DESCRIPTION OF ONE PREFERRED EMBODIMENT OF THE INVENTION

Figure 1:
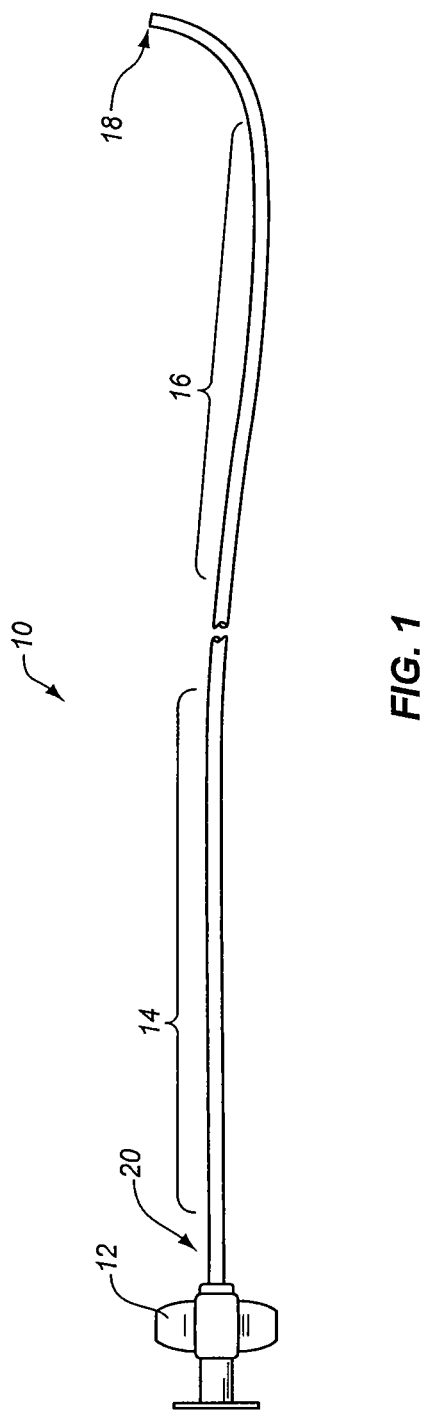
FIG. 1 is a plan view of a completed intravascular catheter.

Referring now to the drawings in greater detail, illustrated in FIG. 1 is a catheter 10, comprising a connecting hub 12, a proximal end 20, a proximal segment or section or portion 14, a distal segment, section or portion 16, and a distal end 18. The completed intravascular catheter 10 is designed and constructed to facilitate introduction into a blood vessel and to support further manipulations to reach the target blood vessel. Manipulation of the catheter 10 is done by the physician, after catheter introduction, external to the blood vessel; that is, the catheter 10 needs to be rotated outside the body, by rotating hub 12 in the proximal segment of the catheter and a corresponding rotational reaction must be achieved in the distal tip 18 inside the body. Therefore, a vascular catheter must transmit torque from the proximal end 20 outside the body to the distal end 18 inside the body.

Figure 2:
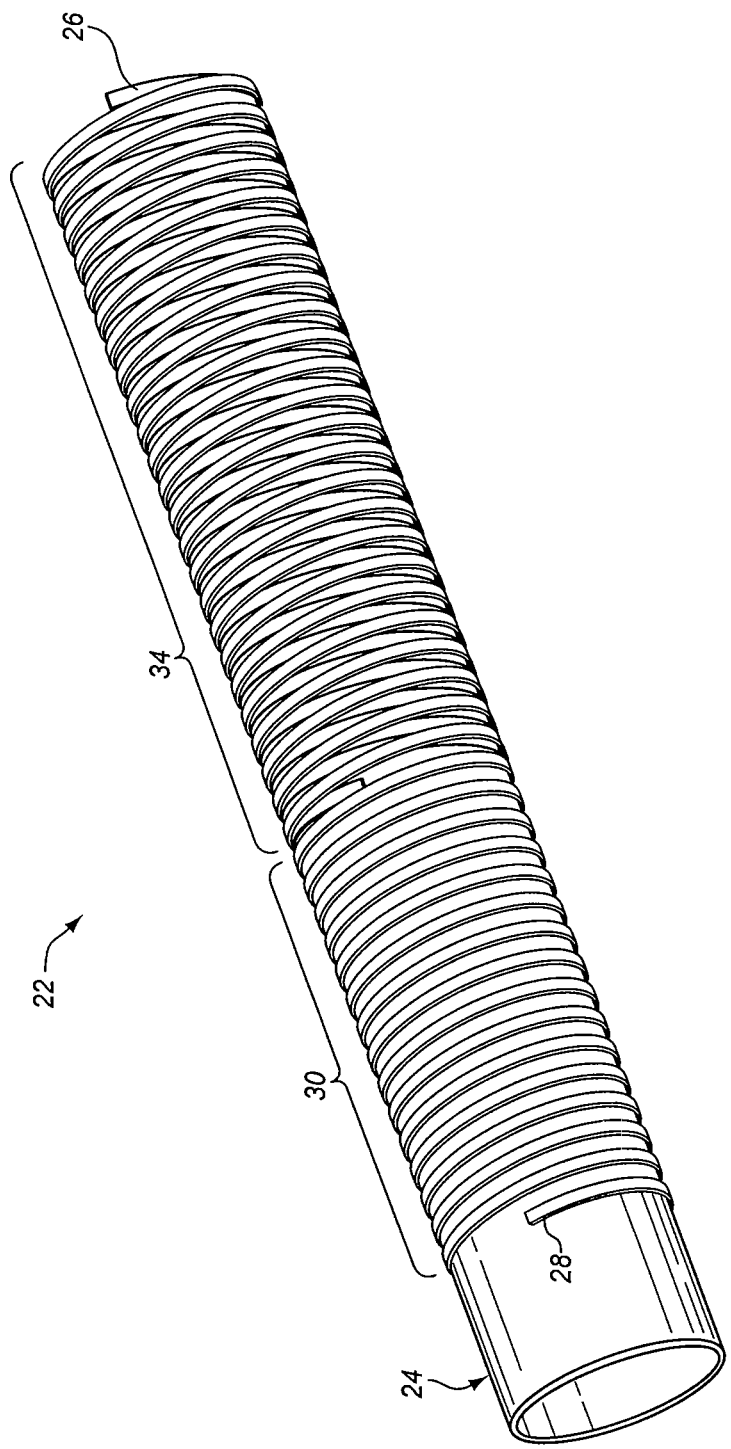
FIG. 2 is a perspective view of an inner tube having a double helix coil on the proximal portion of the inner tube and a single helical coil on a portion of the distal portion of the inner tube.

An internal design 22 of the intravascular catheter is shown in FIG. 2. As shown the design 22 comprises a polymeric inner tube 24, a distal reinforcing segment 30, and a proximal reinforcing segment 34.

The intravascular catheter is used to diagnose and treat a number of medical conditions of the vascular system using a technique called angiography. In addition, smaller catheters, "micro-catheters", are used to infuse certain blood clot dissolving drugs to the coronaries or to brain blood vessels in stroke related cases. Micro-catheters are used successfully for deployment of embolic agents and coils in aneurism within the brain, and therefore the catheter is required to advance forward when pushed, be able to be retrieved when pulled and to rotate when torque is applied as part of the maneuvering process to reach the aneurism. In order to acquire these desirable mechanical characteristics, the internal design and construction of this micro-catheter incorporates the following internal components: a high temperature extruded polymeric inner tube 24, a high stiffness reinforcing jacket 34 comprised of $1^{st}$ layer 26 and $2^{nd}$ layer 28 of helical coiled wire wound over inner tube 24 to form the stiffer proximal reinforcing jacket, and a single layer 28 of helical coiled wire wound over inner tube 24 to form the softer distal reinforcing jacket.

Figure 3:
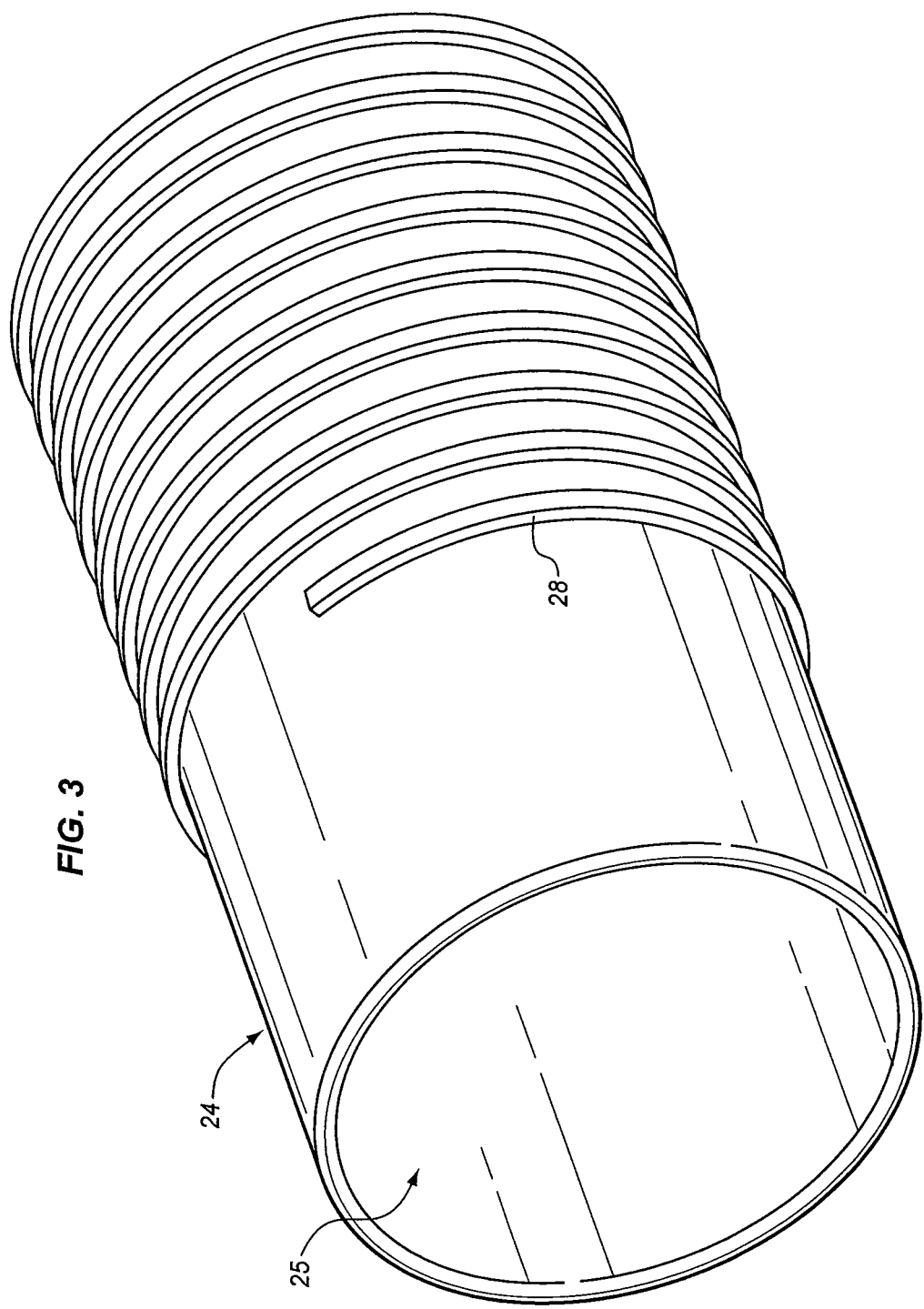
FIG. 3 is an enlarged perspective view of the distal end of the inner tube shown in FIG. 2.

A close-up view of the distal end of the inner tube 24 is shown in FIG. 3 including lumen 25, and the end of the reinforcing flat ribbon wire 28 coiled over the inner tube 24. The inner tube 24 is made of a high temperature fluorinated polymer having a low coefficient of friction, and a flat ribbon stainless steel or platinum tungsten alloy or palladium alloy wire 28 spiraling-coiled over inner tube 24 to form the distal reinforcing jacket. Note that in a micro-catheter application, lumen 25 becomes the delivery conduit to facilitate deployment of embolic agents or coils to blood vessels in the brain, or infusion of blood clot dissolving drugs to the brain or other areas of the vascular system. Likewise, in an angiographic catheter, lumen 25 becomes the delivery conduit to facilitate delivery of contrast media to visualize vasculature using a fluoroscope.

Figure 4:
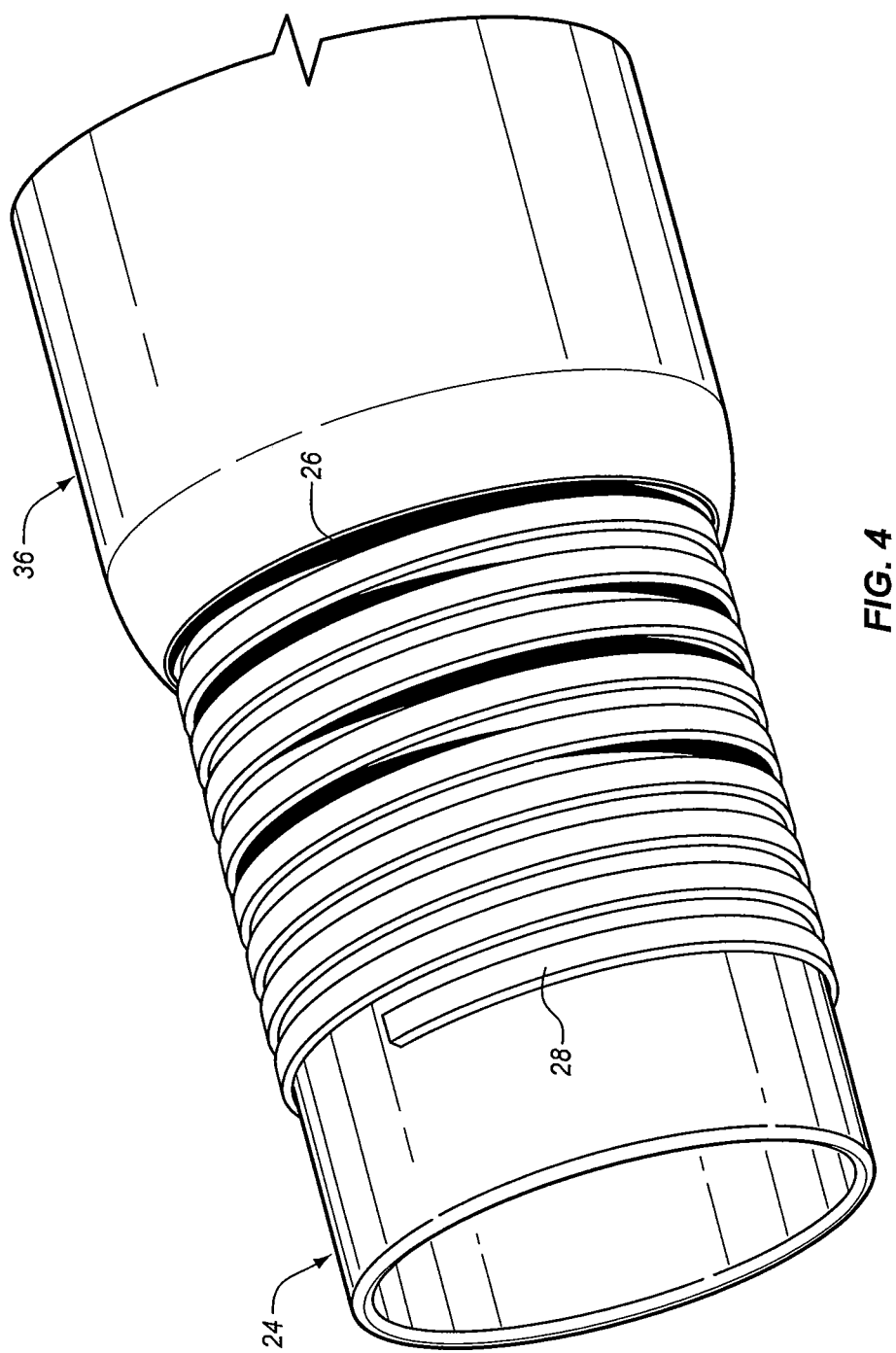
FIG. 4 is a perspective view of a distal end of a catheter constructed according to the teachings of the present invention with a portion broken away and shows the inner tube, the distal helical coil over a portion of a proximal helical coil and a proximal protective outer polymer sheath.

The main components of a "dual segment" catheter design incorporating: the inner tube 24, the distal reinforcing jacket 28 comprising a single layer of coiled wire, the proximal reinforcing jacket comprising dual layers of coiled wire, inner layer 26 and outer layer 28, and the protective outer polymeric sheath 36 is illustrated in FIG. 4. The components of the "dual segment" catheter design include: the polymeric inner tube 24, the distal reinforcing jacket comprising a single layer 28 of helical coiled wire, the proximal reinforcing jacket comprised of $1^{st}$ layer 26 and $2^{nd}$ layer 28 of helical coiled wire, and the outer protective sheath 36 made from low temperature thermoplastic material.

Figure 5:
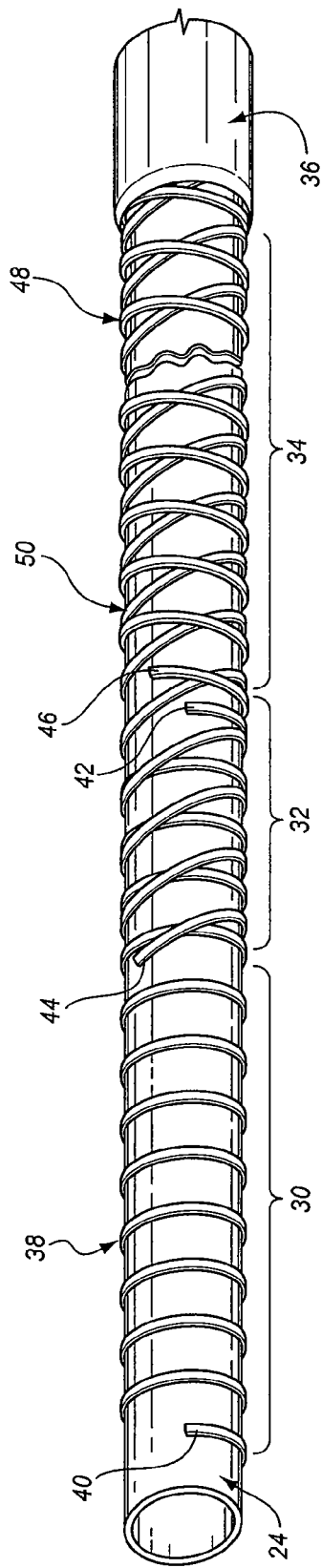
FIG. 5 is a perspective view of the five main components of a catheter constructed according to the teachings of the present invention and shows the inner tube, a platinum ribbon wire helically wound on the distal portion of the inner tube, a 1st stainless steel ribbon wire helically wound proximally on a proximal portion of the inner tube, a $2^{nd}$ stainless steel ribbon wire helically wound distally on the proximal portion and a portion of the protective outer polymer sheath.

The main components of a "triple segment" catheter design is shown in FIG. 5 and includes the inner tube 24, the distal reinforcing jacket 30 comprising a single wire coil 38 made from a material having relatively low stiffness such as platinum or platinum tungsten alloy or palladium alloy, the proximal reinforcing jacket 34 comprising a $1^{st}$ layer of coiled wire 50 under a $2^{nd}$ layer of coiled wire 48, both of these layers made of a relatively stiff material such as stainless steel, the intermediate reinforcing jacket comprising a $1^{st}$ layer of coiled wire 38 (platinum or platinum tungsten alloy or palladium alloy wire) under a $2^{nd}$ layer 50 (stainless steel wire), and the outer protective polymer sheath 36.

With the a "triple segment" catheter design incorporating: the perfluorinated polymeric inner tube 24, the distal reinforcing jacket 30 comprising a single wire coil 38 made from a material having relatively low stiffness such as platinum or platinum tungsten alloy or palladium alloy, the proximal reinforcing jacket 34 comprising a $1^{st}$ layer of coiled wire 50 under a $2^{nd}$ layer of coiled wire 48, both of these layers being made of a relatively stiff material such as stainless steel, the intermediate reinforcing jacket comprising a $1^{st}$ layer of helical coiled wire 38 (platinum or platinum tungsten alloy or palladium alloy wire) under a $2^{nd}$ layer 50 (stainless steel wire), and the outer protective sheath 36 a catheter 10 is created having unique properties. Because the intermediate reinforcing jacket comprises a $1^{st}$ layer of softer platinum or platinum tungsten alloy or palladium alloy wire 38 and a $2^{nd}$ layer of stiffer stainless steel wire 44, the resulting stiffness is approximately halfway between that of the proximal segment or portion 34 and the distal segment or portion 30 reinforcing jackets, thus providing a moderate transition between the two extremes (the stiff proximal reinforcement and soft distal reinforcement), thereby improving the overall compliance and directional stability of the catheter.

In FIG. 5 is illustrated the internal design and construction of a catheter having "Continuously Progressive Compliance" by comprising the perfluorinated polymeric inner tube 24 and a reinforcing jacket 56 comprising one or more spiraling or helical layers of a coiled wire 52 and the outer protective polymer sheath 36. Note that the number of coils per inch is progressively reduced from proximal to distal direction, changing pitch, resulting in a progressively more complaint (less stiff) catheter body from proximal to distal direction. Also note that the entire reinforcing jacket can be manufactured with a single wire material, thus resulting in a more cost effective catheter. While the illustrated embodiment shows a stainless steel wire the outer layer can be made of a different material such as platinum if desired.

Figure 6:
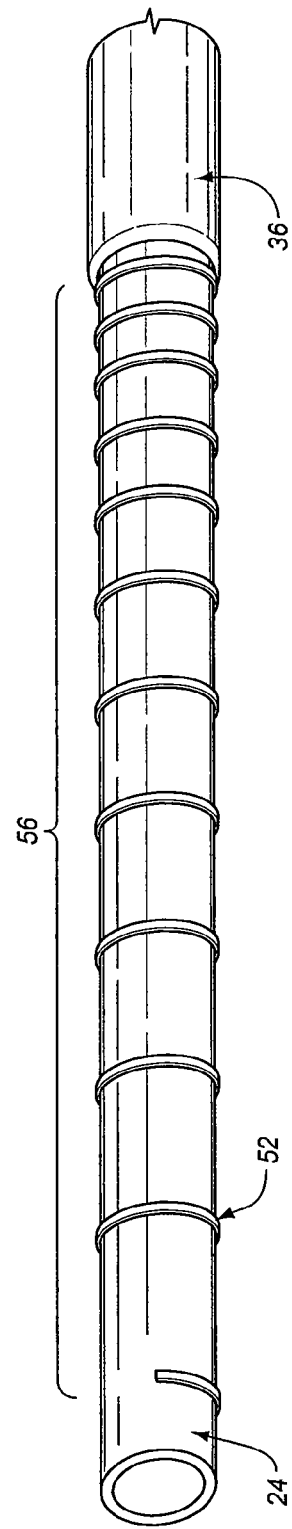
FIG. 6 is a perspective view of a modified distal portion showing the platinum ribbon wire helically wound on the distal portion of the inner tube wound distally with an increasing pitch.

Another improvement to the intravascular catheter involves the use of a selective pitch and or period (cycle) of the helical winding to render a progressively compliant reinforcement of the catheter body and tip as shown in FIG. 6.

Figure 7:
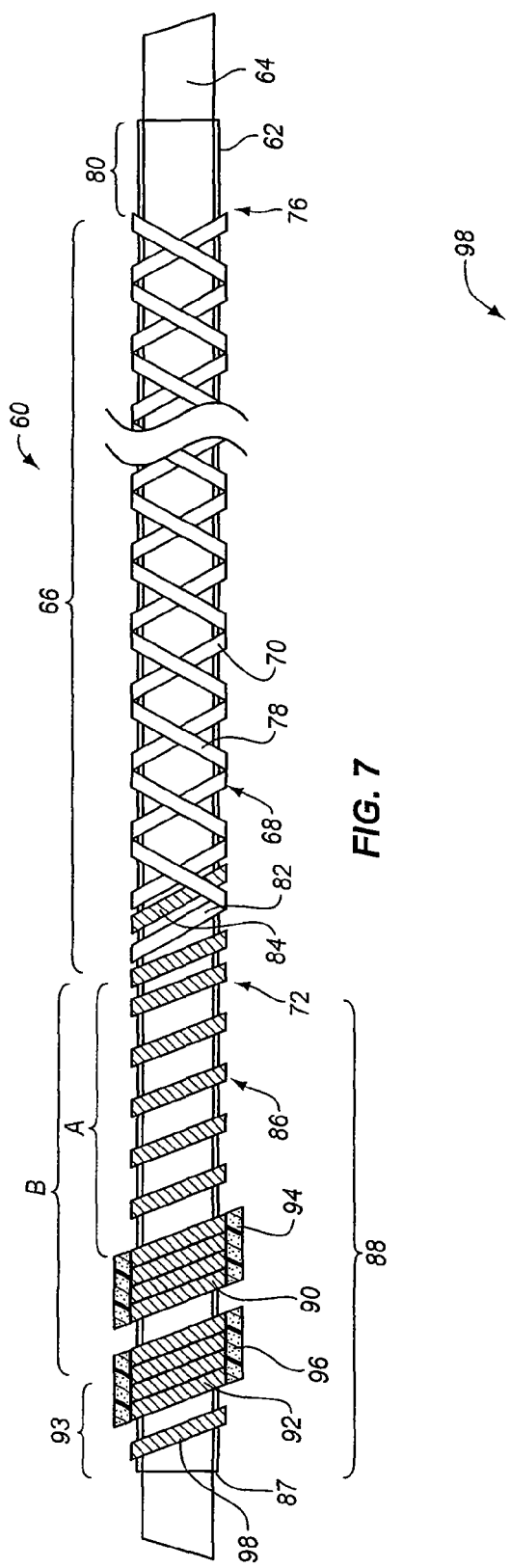
FIG. 7 is a plan view or side elevational view of a partially constructed catheter according to the present invention and shows the inner tube on a mandrel with a platinum ribbon wire wound distally first with a first pitch and then with a second pitch to a first set of four abutting turns, a space on the inner tube and then a second set of four abutting turns, both sets being covered with a film of colloidal tungsten loaded polymer, a $1^{st}$ stainless steel ribbon wire helically wound proximally from an intermediate point proximal of a distal end of the inner tube starting over proximal turns of the platinum ribbon wire proximally to a point close to a proximal end of the inner tube and a $2^{nd}$ stainless steel ribbon wire, being a continuation of the $1^{st}$ stainless steel ribbon wire, wound distally to the intermediate point.

The interior reinforcement of one catheter constructed according to the teachings of the present invention is shown in FIG. 7 and is generally identified with reference numeral 60. The interior reinforcement 60 includes an inner tube liner 62 having an inner lumen and being made of PTFE. The inner tube 62 is shown mounted on a mandrel 64.

A proximal segment, section or portion 66 of the inner tube 62 on which a reinforcing jacket is placed comprises a ribbon wire reinforcement 68 that is wound on the inner tube and that has a length that has a range of approximately 42.3±0.5 to 61.75±0.5 inches. The ribbon wire reinforcement 68 on the segment 66 is a helically wound stainless steel ribbon wire reinforcement 68 comprising a first ribbon wire layer 70 that starts at a distal end 72 of the proximal portion 66 and extends to a proximal end 76 of the first ribbon wire layer 70 on the proximal portion 66. At this point the stainless steel ribbon wire 68 is spirally or helically wound distally in a second outer ribbon wire layer 78 to the distal end 72 of the proximal portion 66. A proximal end segment, section or portion 80 of the inner tube 62 is not reinforced and has a length of approximately 2.9 inches.

A distal portion 82 of the second ribbon wire layer 78 is wound over a beginning portion 84 of a platinum/tungsten flat wire 86 which extends forwardly from just before the distal end 72 of the proximal portion 66 distally towards a distal end 87 of a distal segment, section or portion 88 of the inner tube 62 and which defines a second reinforcing jacket. The platinum/tungsten flat wire 86 can be wound as shown, or can have a change in spacing or variable pitch to a first marker 90 comprising four to nine abutting turns of the platinum/tungsten flat wire 86, with four turns being shown in FIG. 7. A second layer or second and third layers of the platinum/tungsten flat wire may be wound over the first nine abutting turns in order to further enhance radiographic registration of the abutting turns or radiopaque markers. Additionally, the radiographic registration can be further enhanced by heat reflow with either indium or tin-lead solder paste placed directly on the abutting turns.

The pitch of the turns in each layer 70 and 78 of the stainless steel ribbon wire 68 is approximately 0.015" pitch. The pitch of the platinum/tungsten flat wire 86 in a distal portion thereof is approximately 0.010" pitch.

The platinum/tungsten flat wire 86 extends forwardly to the first marker 90 and, depending on the type of catheter, the distance of a section A from the distal end 72 of the proximal portion 66 to the center of the first marker 90 is typically about 21.5±0.2 inches, 5.47±0.2 or 2.5±0.2 inches.

Then, there is a spacing, within the 0.010 pitch zone of approximately 1.2±0.20 inches between the first marker 90 and a second marker 92 of four to nine abutting turns with four turns being shown in FIG. 7 and with a spiral or helical turn or turns between the markers 70 and 78 being hidden from view or not shown.

The markers 90 and 92 have a width of about 0.025±0.002 inch and may contain one layer or two layers of abutting turns.

Each of the markers 90 and 92 is covered with a thin film layer 94, 96 of colloidal tungsten loaded polymer which is shown thicker than it actually is in FIG. 7. Each layer 94, 96 is superimposed over marker 90 or 92 to make the marker more radiopaque. It is to be noted that in some embodiments of the micro-catheter, there is only one marker either at the tip or somewhere in the distal segment.

Again, depending on the type of catheter the distance of a section B from the distal end 72 of the proximal portion 66 to the center of the second marker 92 is about 25±0.5 inch, 6.70±0.5, or 3.75±0.5 inch and the distance of a section 93 from the center of the second marker 92 to the distal end 87 of the inner tube 62 is approximately 2.9 inches. This distance may further be titrated in relation to the type of interventional devise that may be deployed from the microcatheter.

The film layers 94 and 96 are typically made of polyether block amide (PEBAX) loaded with colloidal tungsten powder.

An end turn 98 of the platinum/tungsten flat wire 68 can be provided as shown located approximately 1.3±0.20 inch from the second marker 92.

While ribbon wire or flat wire is illustrated in the drawings, the geometry or cross section of the reinforcement wires 68 and can be round or oval as well as flat. Further mono-filar, bifilar, tri-filar or quadra-filar wire reinforcement can be provided.

Typically, a proximal segment of the inner tube 62 including sections 66 and 80 comprises 62 to 87 percent of the length of the inner PTFE tube 62 and a distal segment including sections B and 93 comprises 13 to 38 percent of the length of the PTFE inner tube 62.

Figure 8:
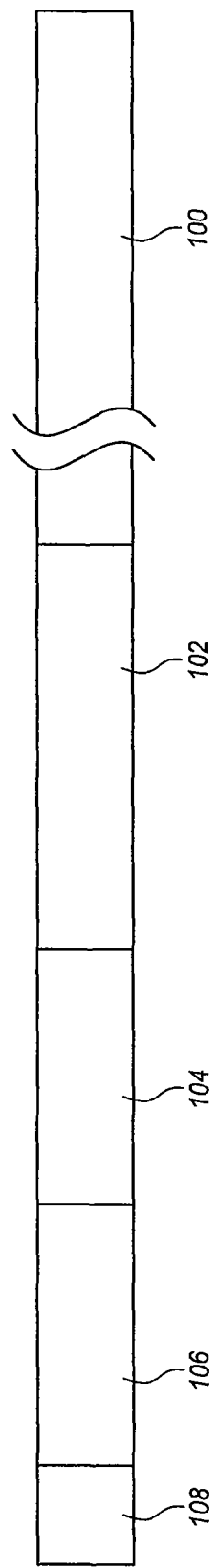
FIG. 8 is plan view or side elevational view of a four segment outer protective polymer sheath which is place over the inner tube and wire reinforcement shown in FIG. 7.

The interior reinforcement 60 is covered with a four section polyether block amide (PEBAX) tube 100 shown in FIG. 8 and including a proximal section 102 made of polyether block amide (PEBAX), a proximal intermediate section 104 made of polyether block amide (PEBAX), a distal intermediate section 106 made of polyether block amide (PEBAX) and a short distal end section 108 constructed according to the teachings of U.S. Pat. No. 5,445,624 and made of polyether block amide (PEBAX). The four sections of polyether block amide (PEBAX) in tube 100 are heat fused over the interior reinforcement 60 of the catheter which in turn bonds to the PTFE inner tube 62.

It will be understood that the inner end portion 84 of the platinum/tungsten portion wire 68 is secured in place by the outer end portion 82 of the second layer 78 of the helically wound stainless steel wire 68. Then the cut ends of the wire forming the markers 90, 92 and the end turn 98 are secured in place by the liners 94 and 96 and by the polyether block amide (PEBAX) tube distal portion 106.

As an alternative, the outer tube or sheath 100 can be extruded over the interior reinforcement 60.

Preferably the proximal reinforcing wire 68 made of stainless steel has end portions softened by an annealing process. The annealing process comprises attaching electrodes to a selected desired end portion, passing a substantial electrical current through the electrodes until the wire end portion glows red hot, and then allowing the wire end portion to slowly return to ambient temperature. This process allows the stainless steel wire to conform to the geometry of PTFE inner tube 62 and prevent the end of wire 68 from springing out of the desired geometry.

Also preferably the proximal reinforcing jacket 68 is made of stainless steel wire 68 which is fed from a spool and the travel speed of the spool holding the stainless steel wire is gradually or periodically increased in order to decrease the number of turns per inch, resulting in a reinforcing jacket having a continuously progressive compliance (softness) from proximal to distal end of the proximal portion of the inner tube 62.

Also according to the teachings of the present invention there is provided a method for manufacturing an intravascular catheter having proximal and distal reinforcing inner jackets, the proximal jacket having superior stiffness and mechanical characteristics than the distal jacket. The method comprising the steps of:

a) Extruding a polymeric PTFE inner tube having an internal lumen, proximal, intermediate and distal segments, and having proximal and distal ends, b) Inserting a mandrel through the internal lumen of the PTFE inner tube, and clamping the mandrel in a bidirectional winding lathe, c) Winding two separate layers of reinforcing helical coiled wire or fibers over the proximal outer surface of the PTFE inner tube, the first layer being wound in a proximal direction starting at a point where the proximal and distal segments meet and terminating at the proximal end, at which point the winding is reversed to a distal direction, thus winding a second layer over the first one, and terminating the layer at the same point where the first coiled wire started, d) Winding a separate reinforcing helical coiled wire over the distal segment, either by start winding in a distal direction at a point where the proximal and distal segments meet and terminating at the distal end, or by start winding in a proximal direction at the distal end and terminating at the point where the proximal and distal segments meet, e) Extruding a polyether block amide polymeric outer sheath over the proximal and distal segments of the PTFE inner tube of the intravascular catheter.

A further method according to the present invention is provided for manufacturing an intravascular catheter inner reinforcement having a proximal section, an intermediate section and a distal section, wherein the proximal section is stiffer than the intermediate section with the intermediate section being softer than proximal section, and the distal section being softer than the intermediate section. The method comprising the steps of:

a) Extruding a perfluorinated polymeric inner tube having an internal lumen, proximal, intermediate and distal segments and having proximal and distal ends, the length of the proximal segment being between 60 and 80% of the total length of the catheter, the length of the intermediate segment being between 10 and 20% the total length of the catheter, and the length of the distal segment being between 10 and 30% of the total length of the catheter, b) Inserting a mandrel through the internal lumen of the inner tube, and clamping the mandrel at both ends in a bidirectional winding lathe, c) Winding a reinforcing wire or fiber helical coil over the intermediate and distal segments, either by starting at the junction between the intermediate and proximal segments and winding in a distal direction until the distal end is reached, or by start winding in a proximal direction from the distal end and terminating at the junction between the intermediate and proximal segments, d) Winding in a proximal direction a new layer of reinforcing helical coiled wire or fiber over the intermediate segment, by starting at the junction between the distal and intermediate segments, and continuing until approximately the entire proximal segment is covered, and then continue winding a second layer in a distal reverse direction and stopping at the junction between the proximal and intermediate segments, thereby forming an intermediate reinforcing layer comprising a first layer of the same stiffer coiled wire or fiber used for the proximal segment on top of a second layer of softer coiled wire or fiber used for the distal segment, thus achieving an intermediate reinforcing segment having a midway stiffness which is between that of the proximal and distal reinforcing segments, and e) Extruding or shrink wrapping a single polymeric outer sheath over the proximal, intermediate and distal segments of the intravascular catheter.

Still further according to the present invention there is provided a manufacturing method for annealing or softening the end of a stainless steel helical coiled wire used to form a reinforcing inner jacket in a catheter, comprising the following steps:

a) Extruding a perfluorinated polymeric inner tube having an internal lumen, b) Inserting a mandrel through the entire lumen of the perfluorinated inner tube, and clamping the mandrel in a bidirectional winding lathe, c) Winding a layer of reinforcing stainless steel helical coiled wire around a desired length of the inner tube, d) Clamping two electrodes between the desired length of the stainless steel end wire to be annealed, e) Clamping a copper heat sink to the catheter side of the stainless steel end wire, f) Momentarily applying sufficient AC or DC current between the electrodes until the stainless steel wire turns red hot, g) Allowing the stainless steel wire to cool down close to ambient temperature.

h) Bending or winding the heat treated stainless steel wires to form a radius compliant with the perfluorinated extruded tube.

From the foregoing description, it will be apparent that the catheter of the present invention and the method for making same have a number of advantages, some of which have been described above and others of which are inherent in the invention.

Also, it will be understood that modifications can be made to the catheter and method of the present invention without departing from the teachings of the invention. For example the wire layers in the proximal wire reinforcement can be made of glass or carbon as well as stainless steel.

Accordingly, the invention is only to be limited as necessitated by the accompanying claims.

What is claimed is:

1. An intravascular catheter comprising:
a polymeric inner tube having an internal lumen and proximal and distal segments;
a distal reinforcing jacket including a first helical coiled wire formed of a first material wound over the surface of said distal segment; and
a proximal reinforcing jacket including a second helical coiled wire and a third helical coiled wire, said second helical coiled wire being formed of a second material wound over the surface of said proximal segment and over said first helical coil, said third helical coiled wire being formed of the second material and wound over said second helical coiled wire and said proximal segment, said second helical coiled wire extending distally beyond said third helical coiled wire, such that said distal reinforcing jacket has a first stiffness, wherein said first stiffness of said distal reinforcing jacket results from said first helical coiled wire alone, said proximal reinforcing jacket has a second stiffness and said first stiffness is relatively lower than said second stiffness, wherein said second stiffness of said proximal reinforcing jacket results from combination of said second and third helical coiled wires, and whereby said first helical coiled wire and said second helical coiled wire overlap to form an intermediate reinforcing jacket having a resulting stiffness approximately halfway between said first stiffness and said second stiffness, and wherein said stiffness of said intermediate reinforcing jacket approximately halfway between said first stiffness from said first helical coiled wire alone and said second stiffness from said combination of said second and third helical coiled wires results from combination of said first and second helical coiled wires.

2. An intravascular catheter comprising:
a polymeric inner tube having an internal lumen and proximal and distal segments;
a proximal reinforcing jacket covering the surface of said proximal segment, said proximal reinforcing jacket comprising a first inner wire layer and a second outer wire layer separate from said first inner wire layer, and said coiled wires of said second outer wire layer being wound over said first layer and being made of a second material, said first inner wire layer of said proximal reinforcing jacket extending distally of said proximal segment;
a distal reinforcing jacket covering the surface of said distal surface, said distal reinforcing jacket comprising a single layer of helical coiled wire formed of a third material, said third material being different from said first material and said first material being relatively stiffer than said third material, such that said distal reinforcing jacket has a first stiffness, wherein said first stiffness of said distal reinforcing jacket results from said single layer of helical coiled wire alone, said proximal reinforcing jacket has a second stiffness and said first stiffness is relatively lower than said second stiffness, said second stiffness of said proximal reinforcing jacket results from combination of said first inner wire layer and said second outer wire layer, and said distal reinforcing jacket extending proximally of said distal segment, whereby said first inner wire layer of said proximal reinforcing jacket and said distal reinforcing jacket overlap to form an intermediate reinforcing jacket having a resulting stiffness approximately halfway between said first stiffness and said second stiffness, and wherein said stiffness of said intermediate reinforcing jacket approximately halfway between said first stiffness from said single layer of helical coiled wire and said second stiffness from said combination of said first inner wire layer and said second outer wire layer results from combination of said first inner wire layer and said single layer of helical coiled wire of said distal reinforcing jacket.

* * * * *